United States Patent [19]

Hayashi et al.

[11] Patent Number: 4,794,195
[45] Date of Patent: Dec. 27, 1988

[54] PROCESS FOR PRODUCING 2,6-NAPHTHALENEDICARBOXYLIC ACID BY OXIDIZING 2,6-DIISOPROPYLNAPHTHALENE

[75] Inventors: Shoichiro Hayashi; Toshiharu Matsuda; Atsushi Sasakawa; Yutaka Konai, all of Iwaki, Japan

[73] Assignee: Kureha Kagaku Kogyo Kabushiki Kaisha, Tokyo, Japan

[21] Appl. No.: 26,322

[22] Filed: Mar. 16, 1987

[30] Foreign Application Priority Data

Mar. 14, 1986 [JP] Japan ................................. 61-56352
Mar. 14, 1986 [JP] Japan ................................. 61-56353
Mar. 14, 1986 [JP] Japan ................................. 61-56355
Mar. 14, 1986 [JP] Japan ................................. 61-56357

[51] Int. Cl.$^4$ ............................................. C07C 51/265
[52] U.S. Cl. ...................................... 562/414; 502/152; 502/229; 502/304; 502/324; 502/325; 562/412; 562/416; 562/417; 562/486; 562/487
[58] Field of Search ............... 562/412, 414, 417, 480, 562/416, 486, 487, 488; 560/77, 78; 502/152, 229, 304, 324, 325

[56] References Cited

U.S. PATENT DOCUMENTS 3,565,945  2/1971  Malmberg et al. .................. 560/77
4,447,646  5/1984  Johnson et al. ..................... 562/487

FOREIGN PATENT DOCUMENTS 142719      5/1985   European Pat. Off. .
1418295   12/1969   Fed. Rep. of Germany .
2428202   12/1974   Fed. Rep. of Germany .
48-54051    7/1973   Japan .
49-133347 12/1974   Japan .
0017453     2/1977   Japan .
1429556     3/1976   United Kingdom .

Primary Examiner—Paul J. Killos
Assistant Examiner—Vera C. Clarke
Attorney, Agent, or Firm—Nixon & Vanderhye

[57] ABSTRACT

Disclosed herein is a process for producing a highly pure produce of 2,6-naphthalenedicarboxylic acid in a large quantity at a moderate price by oxidizing 2,6-diisopropylnaphthalene while using a water-soluble salt of cobalt, a water-soluble salt of maganese or a mixture thereof, a water-soluble salt of cerium and a bromine compound as the catalyst of the oxidation.

16 Claims, 2 Drawing Sheets

PROCESS FOR PRODUCING 2,6-NAPHTHALENEDICARBOXYLIC ACID BY OXIDIZING 2,6-DIISOPROPYLNAPHTHALENE

BACKGROUND OF THE INVENTION

The present invention relates to a process for producing 2,6-naphthalenedicarboxylic acid continuously by oxidizing 2,6-diisopropylnaphthalene. More in detail, the present invention relates to a process for producing 2,6-naphthalenedicarboxylic acid characterized by the process comprising:

(1) step of dissolving 2,6-diisopropylnaphthalene and a catalyst comprising a water-soluble salt of cobalt, a water-soluble salt of manganese or a mixture thereof, a water-soluble salt of cerium and a bromine compound in an aliphatic monocarboxylic acid as the solvent, (2) steps of supplying the obtained solution continuously into a reaction vessel and of oxidizing 2,6-diisopropylnaphthalene by molecular oxygen under an elevated temperature and a pressure, (3) step of drawing the reaction mixture continuously out from the reaction vessel, then depositing and separating crude 2,6-naphthalenedicarboxylic acid crystals from the reaction mixture, (4) step of bringing the separated crystals into contact with an aqueous solution of a mineral acid, thereby dissolving and removing metals of the catalyst from the crystals, (5) step of purifying the crude 2,6-naphthalenedicaboxylic acid crystals, (6) step of adding an alkali carbonate or an alkali bicarbonate to the filtrate of the step of dissolving and removing the metals, thereby depositing and separating the metals as carbonates and/or bicarbonates, (7) step of supplying the separated carbonates and/or bicarbonates of the metals to the step of dissolving 2,6-diisopropylnaphthalene and the catalyst, and (8) step of supplying the filtrate of the step of separating the crude 2,6-naphthalenedicarboxylic acid crystals into the step of dissolving 2,6-diisopropylnaphthalene and the catalyst.

Hitherto, as the process for producing 2,6-naphthalenedicarboxylic acid (hereinafterreferred to as 2,6-NDCA), a process for oxidizing 2,6-dimethylnaphthalene or 2,6-diisopropylnaphthalene by molecular oxygen in acetic acid as the solvent in the presence of a catalyst comprising cobalt and/or manganese and bromine has been known [refer to Japanese Patent Publications No. 48-43893 (1973), No. 56-21017 (1981), No. 59-13495 (1984) and No. 48-27318 (1973) and Japanese Patent Application Laid-Open (KKKAI) Nos. 48-34153 (1973), 49-42654 (1974), 52-17453 (1977), 60-89445 (1985) and 60-89446 (1985)].

Among the processes disclosed in the above references, particularly the following two processes are remarkable:

(1) Process disclosed in Japanese Patent Application Laid-Open (KOKAI) No. 60-89445 (1985):

Process for producing 2,6-NDCA by oxidizing 2,6-diisopropylnaphthalene or its oxidized intermediate with molecular oxygen in a solvent containing at least 50% by weight of an aliphatic monocarboxylic acid of less than 3 carbon atoms, wherein the oxidation of 2,6-diisopropylnaphthalene or its oxidized intermediate is carried out in the presence of a catalyst comprising (i) cobalt and/or manganese and (ii) bromine in the ratio of at least 0.2 mol of the heavy metal to one mol of 2,6-diisopropylnaphthalene or its oxidized intermediate.

(2) Process disclosed in Japanese Patent Application Laid-Open (KOKAI) No. 60-89446 (1985):

Process for producing 2,6-NDCA by oxidizing 2,6-diisopropylnaphthalene or its oxidized intermediate with molecular oxygen in a solvent containing at least 50% by weight of an aliphatic monocarboxylic acid of less than 3 carbon atoms, wherein the oxidation of 2,6-diisopropylnaphthalene or its oxidized intermediate is carried out in the presence of a catalyst comprising (i) cobalt and/or manganese and (ii) bromine and containing cobalt and/or manganese in an amount of at least 1% by weight of the aliphatic monocarboxylic acid of less than 3 carbon atoms.

However, in the above processes, not only a large amount of impurities, for instance, aldehyde derivatives, ketone derivatives, colored substances and nuclear bromides but also the derivatives of phthalic acid and trimellitic acid due to the cleavage of the naphthalene ring are formed, thereby not only the yield of 2,6-NDCA is reduced but also it becomes necessary to provide a complicated purifying process. Moreover, since 2,6-NDCA is obtained with by-products of the oxidation reaction, such as, aldehydes, ketones, brominated derivatives and oxidized polymers of 2,6-NDCA and colored substances, when such 2,6-NDCA is used as a starting material for producing polyethylene 2,6-naphthalate, polyester, polyamide, etc., the degree of polymerization of the polymers become low and the physical properties such as heat-resistance and the appearance such as color of the films and fibers prepared from the polymers are damaged.

Accordingly, as the purifying method of 2,6-NDCA, the following methods have been proposed:

(1) A method comprising the steps of dissolving crude 2,6-NDCA in an aqueous alkali solution, subjecting the solution to thermal treatment for from 1 to 5 hours at a temperature from 100° to 250° C. by stirring thereof, subjecting the solution to decoloring treatment by a solid adsorbent and blowing an acidic gas such as gaseous carbon dioxide or gaseous sulfur dioxide into the solution under a pressure, thereby reducing the pH of the solution and precipitating 2,6-NDCA as a monoalkali salt from the solution [refer to Japanese Patent Publication No. 52-20993 (1977)].

(2) A method comprising the steps of treating an aqueous alkali solution of crude 2,6-NDCA with an oxidizing agent such as alkali perhalogenate or alkali permanganate and blowing gaseous carbon dioxide or gaseous sulfur dioxide into the solution, thereby separating 2,6-NDCA as a monoalkali salt [refer to Japanese Patent Application Laid-Open (KOKAI) No. 48-68554 (1973)], and (3) A method wherein after dissolving crude 2,6-NDCA into an aqueous solution of sodium acetate, condensing the solution and carrying out deposition of crystals, thereby isolating 2,6-NDCA as a monoalkali salt [refer to Japanese Patent Application Laid-Open (KOKAI) No. 50-105639 (1975)].

By the way, words "nuclear bromide(s)" in this application mean an aromatic compounds of which hydrogen(s) of aromatic nucleus is substituted by bromine(s), such as bromobenzene, bromonaphthalene, etc.

However, every one of the above methods of purification is using a method wherein crude 2,6-NDCA is dissolved in an aqueous alkali solution and crystals of the monoalkali salt of 2,6-NDCA are precipitated by adjusting pH of the solution. In the method of purifying crude 2,6-NDCA by adjusting pH of the solution, it is adjusted to from 6.5 to 7.5 by blowing gaseous carbon dioxide or sulfur dioxide under a pressure into an alkali solution of a relatively high concentration of 2,6-NDCA while warming it or by adding a mineral acid to the solution. Then the solution is cooled to 20° C. and the monoalkali salt of 2,6-NDCA is precipitated. The method has a demerit that the composition and the amount of the crystals are variable, are not stable, depending on the conditions such as pH, temperature and concentration, because there exists a delicate equilibrium relationship between the monoalkali salt, dialkali salt and free acid of 2,6-NDCA.

Further, as other carboxylic acids having pKa close to that of 2,6-NDCA are contained in 2,6-NDCA obtained by oxidizing 2,6-dialkylnaphthalene, it is difficult to purify crude 2,6-NDCA to a high purity only by means of adjusting pH. Moreover, it is necessary to wash the crystals with water to remove the mother liquor accompanied, after separating the monoalkalisalt precipitated by pH adjustment. However, since the monoalkali salt of 2,6-NDCA is soluble in water, there is a defect that the rate of recovery of 2,6-NDCA is reduced by the washing.

As it is impossible to purify crude NDCA to a high purity only by crystallization, it is necessary to combine the method of crystallization with other methods such as thermal treatment, oxidative treatment or reductive treatment.

However, when a crystallization is combined with thermal treatment, which makes high temperature and pressure inevitable, oxidative reaction or reductive reaction, there is a problem of numbers of newly formed by-products which become impurities, resulting in a necessity of a means of removing the impurities. Accordingly, the combined method is incomplete as the method of purifying the crude 2,6-NDCA.

Still more, cobalt which is used as a component of the catalyst in the production of 2,6-NDCA is an expensive heavy metal which is relatively difficult to obtain. Accordingly, it is important industrially to reduce the amount of cobalt as small as possible, however, when the amount of cobalt is reduced in the conventional method, the amount of formation of trimetllitic acid, etc. are increased and the yield and purity of 2,6-NDCA are reduced, therefore, it has been recommended to use cobalt in a large amount in the reference.

Moreover, since crude 2,6-NDCA obtained by a conventional method accompanies nuclear bromides [refer, for instance, Japanese Patent Application Laid-Open (KOKAI) No. 48-96573 (1973) and Example 1 of Japanese Patent Application Laid-Open (KOKAI) No. 48-68555 (1973)], from 1000 to 2000 ppm of bromine is usually contained in the product. Also in the present inventors' experiments in the production of 2,6-NDCA by the conventional method, the similar results are obtained and there are many cases wherein from 2000 to 4000 ppm of bromine is contained in the product depending on the reaction conditions. It has been known that the softening point of polyethylene naphthalate produced by using 2,6-NDCA containing large amount of nuclear bromides has been reduced and as a result, quality of the polymer becomes poor.

Furthermore, the conventional process for producing 2,6-NDCA is performed batch-wise, and although possibility of applying a continuous process for producing 2,6-NDCA is suggested, no concrete proposal has been given so far.

In the conventional processes for producing 2,6-NDCA, a large quantity of by-products and decomposed products such as trimellitic acid, aldehydes, colored substances and nuclear bromides is formed, and accordingly a large quantity of heavy metal salt of trimellitic acid and nuclear bromide is contained in the crude 2,6-NDCA and the purity of the crude 2,6-NDCA is usually about 80%. Accordingly, in order to obtain 2,6-NDCA of a purity of higher than 99% from such crude 2,6-NDCA, a complicated purifying method with many steps is necessary, and in addition, since an expensive cobalt has been used in a large amount, the conventional process is unsatisfactory as an industrial process for producing 2,6-NDCA. NDCA.

Moreover, in the method for purifying the crude 2,6-NDCA, a chemical reactions and operations such as condensation, cooling, etc. are performed, therefore, it is impossible to obtain 2,6-NDCA of a high purity in a high rate of recovery.

Still more, in the production of 2,6-NDCA in an industrial scale, since the conventional process is carried out batch-wise, it is impossible to produce a large quanttty of highly pure 2,6-NDCA. Accordingly, an proposal of a continuous process for producing 2,6-NDCA of a purity of higher than 98% in a large quantity has been demanded.

As a result of the present inventors' studies on the process for producing 2,6-NDCA, they have found the way to control the amount of formation of trimellitic acid and nuclear bromides, among many by-products, which give an important influence on the recovery of the heavy metals (cobalt and/or manganese), the re-use thereof and the yield and the purifying steps of 2,6-NDCA while using a far smaller amount of cobalt catalyst than that has been used, and accordingly, the formation of trimellitic acid is suppressed and 2,6-NDCA can be produced in a favorable yield by adding cerium to the catalyst comprising cobalt and/or manganese and bromine. In addition, they have developed the continuous process for producing highly pure 2,6-NDCA in a large quantity and also at a moderate cost, the process is comprising of the following steps:

(1) the step for dissolving 2,6-diisopropylnaphthalene and a catalyst comprising a water-soluble salt of cobalt, a water-soluble salt of manganese or a mixture thereof, a water-soluble salt of cerium and a bromine compound in an aliphatic monocarboxylic acid as the solvent, (2) the step for oxidizing 2,6-diisopropylnaphthalene by molecular oxygen under an elevated temperature and a pressure, while continuously supplying the solution into a reaction vessel, (3) the step for drawing the reaction mixture continuously out from the reaction vessel and precipitating and separating crude 2,6-NDCA from the reaction mixture, (4) the step for bringing the crude 2,6-NDCA crystals separated into contact with an aqueous solution of a mineral acid, thereby dissolving and removing the metals of the catalyst from the crystals, (5) the step for purifying the crude 2,6-NDCA crystals, (6) the step for adding an alkali carbonate or an alkali bicarbonate to the filtrate from the step of dissolving and removing the metals, thereby precipitating and separating the metals as carbonates and/or bicarbonates, (7) the step for supplying the carbonate and/or bicarbonate of the metals to the step for dissolving 2,6-diisopropylnaphthalene and the catalyst, and (8) the step for supplying the filtrate from the step of separating the crude 2,6-NDCA crystals to the step for dissolving 2,6-diisopropylnaphthalene and the catalyst.

On the basis of the above findings, the present inventors have completed the present invention.

SUMMARY OF THE INVENTION

The object of the present invention for producing 2,6-NDCA by oxidizing 2,6-diisopropylnaphthalene lies in reducing the formation of trimellitic acid and nuclear bromides which are the main impurities by adding cerium to cobalt, manganese or a mixture thereof and bromine instead of cobalt, manganese and bromine which are the hitherto-used catalyst. Furthermore, the object of the present invention lies in the evelopment of an industrial process for continuously producing 2,6-NDCA of a high purity in a large quantity at a moderate cost.

Still more, the object of the present invention lies in offering highly pure 2,6-NDCA which is suitable as the raw material for producing polyethylene 2,6-naphthalate, polyester, polyamide, etc. for the production of films and fibers excellent in heat-resistance.

DETAILED DESCRIPTION OF THE INVENTION

The feature of the present invention lies in the process comrrising the first step of dissolving 2,6-diisopropylnaphthalene or its oxidized intermediate and the catalyst comprising a water-soluble salt of cobalt, a water-soluble salt of manganese or a mixture thereof, a water-soluble salt of cerium and a bromine compound in a lower aliphatic monocarboxylic acid as a solvent; the second step of supplying the solution continuously to a oxidation reaction vessel and oxidizing 2,6-diisopropylnaphthalene or its oxidized intermediate with molecular oxygen under an elevated temperature and a pressure; the third step of drawing the reaction mixture out from the reaction vessel continuously and separating the crude 2,6-NDCA crystals deposited by cooling; the fourth step of bringing the deposited crystals into contact with an aqueous solution of a mineral acid, thereby dissolving and separating the solution of metals of the catalyst from the crude 2;6-NDCA crystals; the fifth step of purifying crude 2,6-NDCA and separating pure 2,6-NDCA crystals; the seventh step of adding an alkali carbonate or an alkali bicarbonate to the filtrate of the fourth step, thereby depositing and separating the metals of the catalyst as carbonates and/or basic carbonates and supplying them to the first step and the eighth step of supplying the filtrate of the third step, which separates crude 2,6-NDCA crystals, to the first step.

Of the above-mentioned steps, the first step is the step wherein 2,6-diisopropylnaphthalene or its oxidized intermediate and a catalyst, comprising a water-soluble salt of cobalt, a water-soluble salt of manganese or a mixture thereof, a water-soluble salt of cerium and a bromine compound are dissolved in a lower aliphatic monocarboxylic acid containing less than 30% by weight of water, as a solvent.

"An oxidized intermediate of 2,6-diisopropylnaphthalene" herein mentioned means, of the many intermediates formed by oxidation of 2,6-diisopropylnaphthalene (hereinafter referred to as 2,6-DIPN), the compound which form 2,6-NDCA upon further oxidation.

The compound(s) which can be used as the starting substance in the present invention is (are) the compound(s) shown by the following formula (I):

wherein X is a group selected from the group consisting of and Y is a group selected from the group consisting of —COOH and —CHO.

As the water-soluble salt of cobalt, the water-soluble salt of manganese and the water-soluble salt of cerium, hydroxide, carbonate, halide, salt of aliphatic acids, etc. may be exemplified, however, acetate and carbonate are preferable.

As the bromine compound, hydrogen bromide, hydrobromic acid, alkyl bromides such as methyl bromide, ethyl bromide, etc., alkenyl bromides such as allyl bromide and inorganic salts such as alkali bromides, ammonium bromide, etc. may be exemplified, however, ammonium bromide and cobalt bromide are preferable.

The water-soluble salt of cobalt, the water-soluble salt of manganese and the water-soluble salt of cerium are added so that the total amount of the heavy metals in the catalyst is from 0.01 to 0.15 g-atom, preferably from 0.02 to 0.12 g-atom to 100 g of the solvents, a lower aliphatic monocarboxylic acid containing water. In a case where the catalyst of the heavy metals is used in a large quantity over the above-range, although the yield of 2,6-NDCA is not reduced, the product is accompanied by a large quantity of the heavy metals and purification of the product becomes difficult. On the other hand, in a case where the catalyst of the heavy metals is used in a quantity below the above range, the yield of 2,6-NDCA is reduced, and accordingly such situations are undesirable.

Moreover, the ratio of the water-soluble salt of cobalt, the water-soluble salt of manganese or its mixture to the water-soluble salt of cerium depends on the reaction conditions in the step of oxidation, that is, the reaction temperature, the concentration of the bromine catalyst and the partial pressure of oxygen, therefore the mixing ratio is difficult to predetermine, however, the usual atomic ratio is in the range of 0.03–30, preferably 0.05 to 20, more preferably 0.10–10. When the ratio is over 30, it is absolutely uneconomic and when it is less than 0.03, the reaction speed is so low that the process becomes impractical.

The mixing of the bromine compound is carried out so that the atomic ratio of bromine of the bromine compound to the total heavy metals of the used catalyst is from 0.001 to 1, preferably from 0.005 to 0.6, more preferably from 0.01 to 0.4. When the bromine compound is used over the above range, although the velocity of the oxidation reaction becomes larger, the amount of formation of the nuclear bromides which are difficult to separate from 2,6-NDCA also becomes larger.

The solvent used in the process for producing 2,6-NDCA is a lower aliphatic monocarboxylic acid containing less than 30% by weight of water, preferably from 1 to 20% by weight of water. As the lower aliphatic monocarboxylic acid, those of not more than 4 carbon atoms are preferable and although formic acid, acetic acid, propionic acid and butyric acid may be exemplified, acetic acid is most preferable.

When the starting substance of the pesent invention, that is, 2,6-DIPN or its oxidized intermediate is present at a high concentrtion in the oxidation reaction system, the amount of molecular oxygen supplied to the reaction system is relatively reduced, resulting in the easiness of the progress of side-reactions, and accordingly the yield and the purity of 2,6-NDCA are reduced. Therefore, such a situation is undesirable. Accordingly, it is necessary in the present invention to maintain the concentration of 2,6-DIPN or its oxidized intermediate in the ratio of less than 20 g to 100 g of the solvent.

The second step is a step wherein 2,6-DIPN or its oxidized intermediate is oxidized by molecular oxygen. Molecular oxygen for the reaction is supplied as gaseous oxygen or a mixture of oxygen and an inert gas, however, it is preferable industrially to use compressed air. Although the oxidation reaction proceeds faster as the partial pressure of oxygen in the reaction system is higher, for practical use, the partial pressure of oxygen of from 0.2 to 8 kg/cm$^2$ (absolute pressure) is sufficient for the purpose, and there is no merit in using the partial pressure of oxygen higher than 8 kg/cm$^2$ (absolute pressure). Furthermore, although the total pressure of the gas containing molecular oxygen supplied to the oxidation reaction is not particularly limited, the pressure is preferably used at 2 to 30 kg/cm$^2$ (absolute pressure).

The temperature of the oxidation reaction is from 140° to 210° C., and preferably from 170° to 190° C. When the reaction temperature is over 210° C., it is undesirable because the lower aliphatic monocarboxylic acid is oxidized and decomposed.

In order to suppress the side reactions in the second step, the molar ratio of 2,6-DIPN or its oxidized intermediate to the heavy metals is to be kept under 0.4, preferably under 0.05. It should be noted, however, that with continuous supply of the starting material and the catalyst, and also with high reaction rate to consume the startnng material, the actual molar ratio of the starting material to the heavy metals in the oxidation reactor is always vely low. Accordingly, the requirement on the concentration of the starting material in the second step of the present invention can easily be fulfilled as far as the rate of oxidation is high enough.

In the third step, the separation of the deposited crude 2,6-NDCA crystals is carried out using a separating apparatus such as a centrifugal machine, etc.

The fourth step is a step wherein the separated crude 2,6-NDCA crystals are brought into contact with an aqueous solution of a mineral acid to dissolve and remove the metals of the catalyst. Namely, the separated crude 2,6-NDCA crystals are added to an aqueous solution of sulfuric acid or hydrochloric acid in the concentration of 1 to 10%, preferably 3 to 6% by weight while stirring and the pH of the solution is adjusted to from 1 to 3, preferably from 1 to 2, thereby dissolving out heavy metals of the catalyst from the crude 2,6-NDCA crystals.

The fifth step is a purifying step of the crude 2,6-NDCA, and is performed by one of the following three methods.

(1) The crude 2,6-NDCA is dissolved in an aqueous solution of an alkali such as sodium hydroxide, potassium hydroxide, sodium carbonate and potassium carbonate, the pH of the aqueous solution being higher than 9, preferably higher than 11, and into the alkali solution of 2,6-NDCA, a water-soluble neutral salt of the same cation as that used in the aqueous alkali solution (hereinafter referred to as the common cation) is added so that the formed solution contains 10 to 30% by weight, preferably 15 to 25% by weight of the water-soluble neutral salt, and the solution is stirred at a temperature of from 10° to 100° C., preferably from 20° to 50° C. to precipitate 2,6-NDCA as a dialkali salt.

(2) The crude 2,6-NDCA is added to an aqueous solution containing an amount of more than neutralizing amount of an alkali, such as sodium hydroxide, potassium hydroxide, sodium carbonate and potassium carbonate, and 10 to 30% by weight, preferably 15 to 25% by weight of a water-soluble neutral salt of the common cation therewith, and the mixture is stirred at a temperature of from 10° to 100° C., preferably from 20° to 50° C., to precipitate 2,6-NDCA as an alkali salt.

(3) The crude 2,6-NDCA is added to methanol at a molar ratio of methanol to 2,6-NDCA greater than 15, preferably from 20 to 70, and the mixture is heated to a temperature in the range of 110° to 140° C., preferably 120° to 135° C. under stirring, and then concentrated sulfuric acid was added to the heated mixture to esterify 2,6-NDCA.

After the reaction is over, the reaction mixture is cooled to precipiaate the crystals of dimethyl ester of 2,6-NDCA in a purified form.

The water-soluble neutral salt of the common cation means a water-soluble neutral salt of alkali metal such as sodium or potassium which dissolves in water at 20° C. in an amount of more than 10% by weight, preferably more than 15% by weight, and sodium chloride, potassium chloride, sodium sulfate, potassium sulfate, sodium nitrate and potassium nitrate may be exemplified.

The amount of addition of the water-soluble neutral salt is limited to from 10 to 30% by weight, preferably from 15 to 25% by weight of the solution subjected to the treatment of salting out, namely, the cation concentration is not higher than 10 mol/liter, preferably not higher than 5 mol/liter and also should be less than the solubility of the neutral salt. When the water-soluble neutral salt is added over its solubility, it is not desirable, because the neutral salt not dissolved mix with the salted-out crystals. Furthermore, even when the water-soluble neutral salt is added so that the concentration of the cation is over 10 mol/liter, the effect of salting out is not improved, and since the specific gravity and the viscosity of the aqueous solution is raised, the solid-liquid separtion becomes difficult.

The solubility of dialkali salt of 2,6-NDCA into the aqueous solution is rapidly reduced when the concentration of the common cation, for example, sodium ion in the case of disodium salt and potassium ion in the case of dipotassium salt, is increased.

For instance, the solubility of 2,6-NDCA.2Na at 20° C. in the aqueous solution, of which sodium ion concentration is 1.5 mol/liter prepared by adding sodium chloride to an aqueous sodium hydroxide solution of pH 12, is about 11% by weight and when the concentrations of sodium ion are 2.2, 3, 4 and 5.4 mol/liter, the solubilities are about 7, 1.7, 0.4 and 0.2% by weight, respectively.

In this specification, "2,6-NDCA.dialkali" means dialkali salt of 2,6-NDCA and "2,6-NDCA.2Na" and "2,6-NDCA.2K" mean disodium and dipotassium salt of 2,6-NDCA, respectively.

In the step of salting out, the amount of alkali larger than neutralization equivalent is enough just for salting-out 2,6-NDCA, however, to precipitate and remove the minute amount of heavy metals, contained in crude 2,6-NDCA, as hydroxide or oxide, it would probably be desirable to use the alkali in an amount of more than 1.2 times of the neutralization equivalent while holding the pH of the aqueous solution at higher than 9, preferably higher than 11. The concentration of alkali is from 2 to 10% by weight, preferably from 4 to 7% by weight.

In the step of salting out, the amount of the water-soluble neutral salt to be added and the concentration of 2,6-NDCA.dialkali are adjusted in a broad range according to the desired purity and the desired rate of recovery of 2,6-NDCA, therefore, the concentration of each compound is decided mutually in relation to the concentration of the cation present in common, however, as for the concentration of crude 2,6-NDCA, 50 to 250 g/liter, preferably 110 to 180 g/liter is practical from the viewpoint of the operation for purification.

The sixth step is a step only necessary in the method of purifying by salting out, and is not necessary in the purification by the esterification of 2,6-NDCA. Namely, the sixth step is a step of precipitating 2,6-NDCA crystals by adding 2,6-NDCA.dialkali into a mineral acid and making the pH of the obtained aqueous solution to lower than 4, preferably to 2 to 3. Namely, the crystals of 2,6-NDCA.dialkali which have been salted out at the fifth step are added into a solution of a mineral acid such as sulfuric acid, hydrochloric acid or nitric acid, the concentration of 2,6-NDCA.dialkali being from 5 to 60% by weight, preferably from 20 to 40% by weight, and the pH of the solution is adjusted to lower than 4, preferably from 2 to 3 to precipitate 2,6-NDCA free acid. By carrying out the solid-liquid separation of the crystals of 2,6-NDCA using a separator, 2,6-NDCA of a purity of higher than 98% is obtainable.

There is the seventh step wherein an alkali carbonate or an alkali bicarbonate is added to the filtrate of the fourth step to separate the metals of the catalyst as carbonates and/or basic carbonates and are returned to the first step, and there is the eighth step wherein the filtrate of the third step is recycled to the first step.

In the seventh step, a solution of an alkali carbonate, such as sodium carbonate and potassium carbonate or a solution of an alkali bicarbonate such as sodium bicarbonate and potassium bicarbonate of a concentration from 1 to 34% by weight, preferably from 15 to 25% by weight is added to the filtrate of the fourth step, and its pH is adjusted to 7 to 10, preferably 7.5 to 9.5 to recover the metals of the catalyst as carbonates and/or basic carbonates and the recovered carbonates and/or basic carbonates are returned to the first step (step of dissolving). Accordingly, the additional supply of the metals of the catalyst is usually not necessary.

By providing a reflux condenser and a distilling tower at the top of the vessel for oxidation reaction, it is possible to discharge water formed by the oxidation reaction to outside of the system and to reflux the lower aliphatic monocarboxylic acid accompanied by the water.

Futheremore, after washing the crude 2,6-NDCA crystals obtained in the third step with a lower aliphatic acid such as acetic acid, propionic acid and butyric acid, which contains less than 30% by weight of water, thereby removing the impurities such as manganese trimellitate from the crystals, the washed crude 2,6-NDCA crystals are heated to a temperature higher than the boiling point of the lower aliphatic monocarboxylic acid and lower than 200° C. to recover the lower aliphatic monocarboxylic acid accompanied by the crystals. In the case where the lower aliphatic monocarboxylic acid is acetic acid, the thermal treatment is carried out at a temperature of 120° to 200° C., preferably 130° to 160° C.

Moreover, a part of the filtrate in the eighth step is supplied to a dehydrating tower and after removing by-produced water in order to control the water-balance in the system of oxidation reaction, the part of filtrate can be returned to the first step.

Still more, it is possible to send a part of the filtrate treated in the dehydrating tower to a distillation for recovery of the lower aliphatic monocarboxylic acid, to recycle the recovered lower aliphatic monocarboxylic acid to the first step of dissolving the starting substances and to send the rest of the recovered solvent to the third step of washing the crude 2,6-NDCA crystals.

By subjecting the 2,6-NDCA crystals obtained to the following treatment, the coloring substances can be removed therefrom and accordingly, the purity of the product can be further improved:

(1) A method of treatment wherein an aqueous solution, to which the crystals of 2,6-NDCA.dialkali separated in the fifth step has been dissolved, is subjected to adsorption treatment with activated carbon.

(2) A method of treatment wherein an aqueous alkali solution of the crude 2,6-NDCA crystals is obtained in the first half of the fifth step, is subjected to adsorption treatment with activated carbon.

For use in the above treatments, any shape and form of activated carbon may be used, such as particle, granule, globule, crushed form and powder, however, the powdery activated carbons of a large surface area acts effectively.

A method of treatment with activated carbon is concretely explained as follows.

In case of carrying out the treatment with activated carbon after salting out in the fifth step, activated carbon may be directly added to an aqueous solution of 2,6-NDCA.dialkali and after stirring the solution for more than 30 minutes, activated carbon is separated from the solution, however, in order to utilize activated carbon effectively, it is preferable to pass the solution through a layer filled up with activated carbon for carrying out the adsorptive treatment.

The temperature at which the adsorptive treatment is performed with activated carbon is from 5° to 100° C., preferably from 10° to 30° C. Moreover, when sodium chloride is present in an amount of from 1 to 3% by weight in the aqueous solution of 2,6-NDCA.dialkali, the adsorptive activity of activated carbon is increased, accordingly it is possible to reduce the amount of activated carbon used for the purpose of purification. For instance, (1) crude 2,6-NDCA is dissolved in an auueous solution of sodium hydroxide, (2) the solution was subjected to salting out by using sodium chloride, (3) the obtained crystals are washed with an aqueous solution of sodium chloride, and (4) the crystals are dissolved in water, then an aqueous solution of 2,6-NDCA containing sodium chloride in a suitable concentration for the adsorption can be obtained. When such solution is treated with activated carbon, the consumption of activated carbon can be reduced.

By carrying out this adsorptive treatment after the salting-out step, it is possible to obtain colorless 2,6-NDCA of a purity of higher than 99.8%.

Further, the residue obtained from the bottom of the monocarboxylic acid recovering tower, can be supplied to the seventh step together with the filtrate from the fourth step.

Still more, since the filtrate of salting out, from which 2,6-NDCA.dialkali has been separated in the fifth step, contains the impurities dissolved therein, the dissolved impurities are deposited and removed by adding a mineral acid having the same anion as that of the water-soluble neutral salt used in the salting-out step adjusting the pH of the solution below 3. Then, the concentration of the salt and the pH of the solution from which the impurities have been removed are adjusted, and the solution is circulated to the step of salting out. By such a circulation of the filtrate, the additional supply of the water-soluble neutral salt becomes unnecessary in usual cases.

Accordin to the process for producing 2,6-NDCA of the present invention, the atomic ratio of the amount of cobalt used to the amount of cerium used is from 0.03 to 30, and by using such an amount of cerium, it becomes possible to reduce the amount of trimellitic acid and the bromides of naphthalene ring which are difficult to remove from the product by purification.

Furthermore, the purity of crude 2,6-NDCA obtained according to the present invention is higher than 85% by weight, and accordingly, the complexity of the purification step can be remarkably reduced as compared with the conventional process. Particularly, since the content of the heavy metal salt of trimellitic acid in crude 2,6-NDCA is less than 5% by weight, the recovery and the re-use of the heavy metal can be performed remarkably more easily than in the conventional process for producing 2,6-NDCA.

Still more, although the amount of elementary bromine contained in crude 2,6-NDCA obtained by the conventional process, is from 1000 to 4000 ppm, the amount can be reduced to less than 300 ppm according to the process of the present invention. Accordingly, by purifying crude 2,6-NDCA obtained by the present process, 2,6-NDCA of a purity of higher than 98%, of a content of elementary cobalt of less than 3 ppm, of a content of elementary manganese of less than 3 ppm, of a content of elementary cerium of less than 3 ppm, of a content of bromine of less than 3 ppm and of an optical density of less than 0.03 can be continuously obtained. By subjecting the thus purified 2,6-NDCA further to the adsorptive treatment by activated carbon, 2,6-NDCA of a purity of higher than 99.8%, each of the contents of elementary cobalt, managanese and cerium being less than 2 ppm, respectively, and of the content of bromine of less than 2 ppm and of the optical density of less than 0.02 can be obtained continuously.

In this connection, when the whiteness of a polyester chip obtained by polycondensing ethylene glycol and 2,6-NDCA produced by the present invention is measured with a color difference meter, the value of Hunter scale b is 1.6, namely, a polymer excellent in the whiteness can be obtained by using 2,6-NDCA manufactured by the present invention.

Moreover, according to the process of the present invention, the waste discharged from the system of the process is mainly water, removed from the substances containing water, and the metals of the catalyst and the lower aliphatic monocarboxylic acid are re-used in circulation and maintained inside of the system.

Furthermore, as 2,6-NDCA.dialkali is hardly soluble in an aqueous solution of a water-soluble neutral salt of the common cation, it is possible to wash 2,6-NDCA.-dialkali by an aqueous solution of a suitable concentration of the water-soluble neutral salt, and since the impurities dissolved in the mother liquor and the washings of the salting-out step can be easily removed by adding a mineral acid, the treated mother liquor and washings can be re-used in circulation without causing any accumulation of the impurities, and usually, the additional supply of the water-soluble neutral salt is unnecessary.

Figure 1:
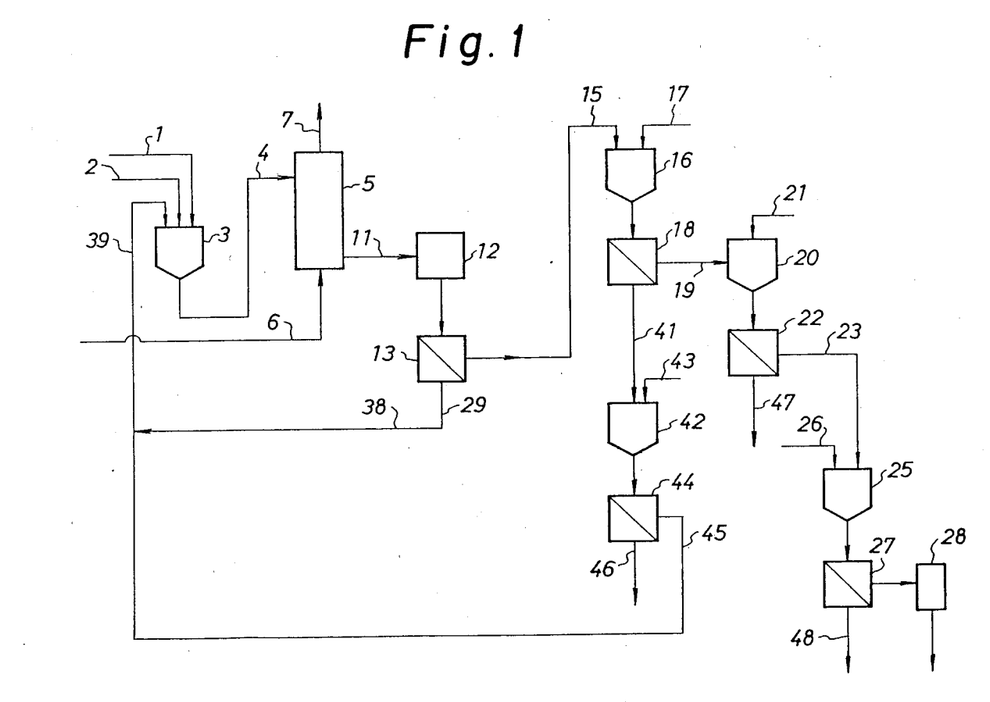
FIG. 1 is a block flow-chart of a continuous manufacturing process for 2,6-NDCA according to the present invention

In FIG. 1 of the attached drawings, 2,6-DIPN is supplied through the feed line (1) of 2,6-DIPN to the dissolving vessel (3) of the raw materials, and acetic acid and catalyst mixture are supplied via the feed line (2) to the vessel (3), and 2,6-DIPN is dissolved in acetic acid therein. In the next place, the acetic acid solution of 2,6-DIPN and the catalyst is continuously supplied to a reaction vessel (5) (for oxidation, titanium-lined and operated under a pressure) equipped with a stirrer via the raw material feed line (4).

Into the reaction vessel (5), compressed air is introduced via the feed line (6). The exhaust gas from the reaction vessel (5) is released to outside of the system through the line (7) after acetic acid is recovered.

The oxidation product is continuously drawn from the reaction vessel (5) via the line (11) and sent to the flash vessel (12), the pressure of the reaction is reduced to ordinary level in the flash vessel (12) and the temperature of the oxidation product goes down to 90° to 110° C. The solid matter comprising the crude 2,6-NDCA crystals deposited in the flash vessel is isolated by a centrifugal separator (13).

The obtained crude 2,6-NDCA crystals are conveyed to the catalyst extracting vessel (16) via the feed line (15). Into the catalyst extracting vessel (16), a mineral acid is introduced through the line (17) and the mixture is stirred in the vessel (16) at a temperature of 80° to 90° C. After finishing the extraction of the heavy metals, the slurry in the vessel (16) is sent to a centrifugal separator (18) and subjected to solid-liquid separation therein and the solid (crude 2,6-NDCA) is washed well with hot water of 80° C.

The washed crude 2,6-NDCA is conveyed to the salting-out vessel (20) via the line (solid matter conveyer) (19) for drawing out crude 2,6-NDCA from the separator (18). Into the salting-out vessel (20), sodium chloride and sodium hydroxide are supplied via the feed line (21), and the mixture is stirred in the vessel (20) at a temperature of 25° to 35° C. The resulting slurry is filtered by the separator (filter press) (22) and the solid matter is washed with an aqueous solution of sodium chloride.

The washed solid matter (2,6-NDCA.dialkali) is introduced into the acid-treating vessel (25) via the conveying line (23). Into the acid-treating vessel (25), sulfuric acid is continuously supplied through the feed line (26) adjusting the pH of the solution in the vessel (25) to not more than 4, preferably 2 to 3. After carrying out solid-liquid separation in a separator (filter press) (27) for purified 2,6-NDCA, the solid matter is washed until the chloride ion is not detected in the washings and then continuously dried in a drier (28) at a temperature of 120° to 150° C. to obtain 2,6-NDCA of a high purity continuously.

On the other hand, the filtrate from the centrifugal separator (13) is recycled to the dissolving vessel (3) via the drawing line (29), the line (38) and the recycling line (39).

The filtrate of extraction which is sulfuric acid-acidic and contains the heavy metals of the catalyst is led to a separating vessel (42) via the line (41). Into the separating vessel (42), an aqueous solution of sodium carbonate is continuously supplied through the feed line (43), and the pH of the solution in the vessel (42) is adjusted from 7 to 10 to deposit the carbonates and/or basic carbonates of cobalt, manganese and cerium. The carbonates and/or basic carbonates of the heavy metals are subjected to solid-liquid separation in the centrifugal separator (44). The filtrate is neutralized and discharged to outside of the system via a line (46) and the catalysts are washed with water and returned to the dissolving vessel (3) via the line (45) and the line (39).

The filtrate of salting-out step is subjected to removal of the impurities and then discharged to outside of the system via the line (47). The filtrate from the separator (27) is neutralized and then discharged to outside of the system through the line (48).

Figure 2:
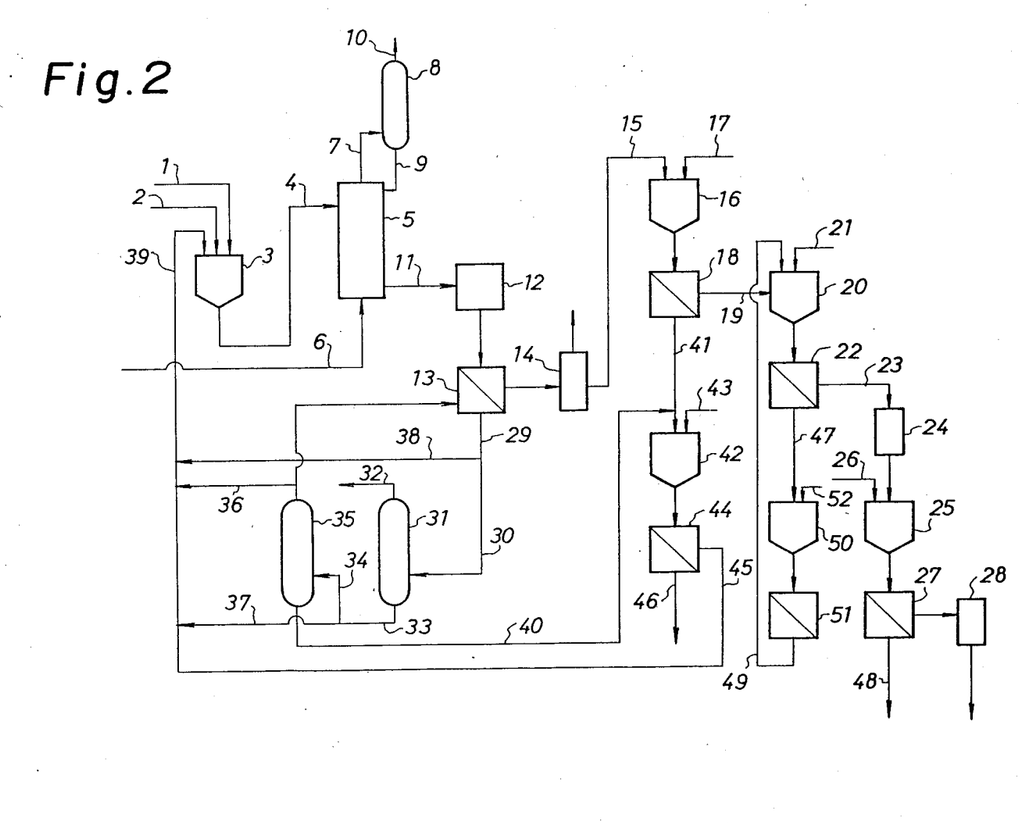
FIG. 2 is a block flow-chart of preferable embodiment thereof.

The preferable mode of operation will be explained while referring to FIG. 2 of the drawings as follows.

Into the dissolving vessel (3), 2,6-DIPN is supplied through the feed line (1), and acetic acid and the catalyst mixture are supplied from the feed line (2) and 2,6-DIPN is dissolved in the vessel (3). In the next place, an acetic acid solution of 2,6-DIPN and the catalyst is continuously supplied to the reaction vessel (5) equipped with a reflux condenser (8) and a stirrer via the feed line (4). Into the reaction vessel (5) operated under a pressure, compressed air is introduced via the feed line (6). The exhaust gas from the reaction vessel (5) is led to the reflux condenser (8) via the line (7) and cooled therein. Acetic acid contained in the exhaust gas is recycled to the reaction vessel (5) via the line (9), and the exhaust gas is discharged to outside via the line((10).

The oxidation product is continuously drawn out via the line (11) and the pressure of the oxidation reaction is reduced to ordinary level in the flash vessel (12) and the temperature of the oxidation product goes down to 90° to 110° C. The solid matter comprising crude 2,6-NDCA is separated by the centrifugal separator (13) and the crude 2,6-NDCA is washed with hot actic acid, the acetic acid used in washing being separated and recovered in a drying tower (14).

The dried crude 2,6-NDCA is conveyed to the catalyst extraction vessel (16) via the feed line (15). Into the catalyst extracting vessel (16), a mineral acid is supplied through the line (17), and the mixture in the vessel (16) is stirred at a temperature of 80° to 90° C. After finishing the extraction, the slurry is subjected to solid-liquid separation by the centrifugal separator (18), and the solid matter is washed well with hot water at 80° C.

The washed crude 2,6-NDCA is conveyed to the salting-out vessel (20) via the line (solid matter conveyer) (19) for drawing out crude 2,6-NDCA from the separator (18). Into the salting-out vessel (20), a recovered filtrate containing a water-soluble neutral salt of an alkali metal is supplied through the line (49) and an aqueous solution of sodium chloride and an alkali hydroxide is supplied through the feed line (21). The materials in the salting-out vessel are stirred at a temperature of 25° to 35° C. After filtering the slurry formed by salting out by the separator (filter press) (22), the solid matter (2,6-NDCA.dialkali) is washed with an aqueous solution of sodium chloride.

The obtained 2,6-NDCA.dialkali is dissolved in warm water and introduced into the decolorizer (24) for treatment with activated carbon via the line (23), and subjected to decoloring treatment in the vessel (24). The decolored solution is introduced into the acid-treating vessel (25). Into the vessel (25), sulfuric acid is continuously supplied through the feed line (26) and the pH of the solution in the vessel (25) is adjusted to not more than 4, preferably 2 to 3. After carrying out the solid-liquid separation in the separator (27) (filter press), the solid matter (purified 2,6-NDCA) is washed with water until no chloride ion is detected and then continuously dried by the dryer (28) at a temperature of 120° to 150° C. to obtain 2,6-NDCA of a high purity continuously.

Further, as in FIGS. 1 and 2, only the method of purification performed by salting out is described, the case where the purifying is performed by the dimethyl ester method will be explained as follows.

The crude 2,6-NDCA washed by hot water in the centrifugal separator (18) is conveyed to the vessel for esterification and is mixed with methanol, and after the addition of sulfuric acid to the mixture, the esterification is carried out in the vessel. The crystals precipitated upon cooling the reaction mixture are subjected to solid-liquid separation and after washing with methanol, the crystals are dried in a drier to obtain the refined dimethyl ester of 2,6-NDCA.

After neutralizing the filtrate with an alkali, for instance, sodium hydroxide or calcium carbonate, the insoluble matters in the neutralized filtrate are separated and removed, and the treated filtrate is subjected to distillation in a methanol-recovering tower. A part of the recovered methanol is used for washing of dimethyl ester of 2,6-NDCA and the rest is used in the vessel for esterification in circulation.

Backing to the explanation of the drawings, the filtrate from the centrifugal separator (13) is, via the drawing line (29) of the oxidation filtrate, partly returned to the dissolving vessel (3) via the line (38) and the recycle line (39) and the rest of the filtrate is introduced into the dehydrating tower (31) via the line (30) and the water formed by oxidation of 2,6-DIPN is discharged to outside via the drawing line (32). The liquid from which water has been removed is drawn out from the dehydrating tower (31) through the line (33) and a part of the liquid is returned to the dissolving vessel (3) via the line (37) and the recycle line (39). The rest of the liquid is led to the acetic acid-recovering tower (35) via the line (34) for the recovery of acetic acid. A part of the recovered acetic acid is used for washing the cake in the centrifugal separator (13) and the rest of the recovered acetic acid is recycled to the dissolving vessel (3) via the line (36) and the recycle line (39).

The residue remaining at the bottom of the acetic acid-recovering tower (35) contains a part of the heavy metals of the catalyst and organic by-products which are alkali-soluble, and is introduced into the vessel (42) via the line (40) to recover the heavy metals.

The extraction filtrate which contains the heavy metals of the catalyst and is sulfuric acid-acidic is led to the vessel (42) for separating the heavy metals via the line (41). Into the vessel (42), an aqueous solution of sodium (bi)carbonate is continuously added through the feed line (43) and the pH of the solution in the vessel (42) is adjusted to from 7 to 10 to precipitate the carbonates and/or basic carbonates of cobalt, manganese and cerium. The precipitate is subjected to solid-liquid separation by the separator (centrifugal separator) (44). The separated filtrate is discharged to outside via the line (46) and the solid (catalyst) is washed with water and recycled to the dissolving vessel (3) via the lines (45) and (39).

The filtrate of salting out is introduced into the acid-treating vessel (50) via the line (47). Into the vessel (50), a mineral acid is supplied through the line (52), and the pH of the mixture in the vessel (50) is adjusted to lower than 3 while stirring the mixture. After subjecting the mixture to solid-liquid separation by the centrifugal separator (51) to remove the solidified impurities, the filtrate from the separator (51) is returned to the salting-out vessel (20) via the line (49). The filtrate from the separator (27) for purified 2,6-NDCA is neutralized and then discharged to outside via the line (48).

The process for producing 2,6-NDCA according to the present invention will be concretely explained while referring to the following non-limitative Examples. In Example 1 and Comparative Example, the oxidation of 2,6-DIPN was carried out batchwise for showing the effect of cerium clearly and crude 2,6-NDCA formed was analysed.

Examples 2 and 3 are examples showing the continuous process for producing 2,6-NDCA according to the present invention, and Example 4 explains the method for purifying the crude 2,6-NDCA by the methyl ester process.

Further, the quantitative analyses of 2,6-NDCA and trimellitic acid were carried out by the high performance liquid chromatography, and the quantitative analyses of the heavy metals were carried out by the ICP analytic method. The elementary analysis of bromine was carried out by x-ray fluorescence analytical method and the colored material was analyzed by the OD value (500 nm) of the solution in methylamine.

(1) High performance liquid chromatography

Apparatus: HPLC analytical apparatus made by Waters Co., Model 510
Column: A connected column consisting of Lichrosorb ® (5 μm, made by Merck Co.) and Radial-pack ® cartridge C-8 (made by Waters Co.)
Moving phase: a 45:55 (by volume) mixture of water of pH 3 and acetonitrile and of a flowing speed of 0.6 cc/min.
Internal standard substance: 2-naphthoic acid
Wave length for detection: 260 nm.

(2) X-ray fluorescence analytical method

Apparatus: X-ray fluorescence analytical apparatus (made by RIGAKU-DENKI Co., Model 3080 E 2)
X-ray tube: Rhodium (under 50 KV and 50 mA)
Detector: PC detector
Crystals: Germanium The specimen (10 g) was processed into tablets of 30 mm in diameter and subjected to the analysis.
Detection limit: 3 ppm.

(3) Analysis of the colored component:

Into 10 ml of an aqueous 25% solution of methylamine, 1 g of a specimen was dissolved, and the optical density of the solution was measured in a quartz cell of 10 mm thickness with the light of 500 nm in wave length.

EXAMPLE 1

Into a titanium lined stainless-steel autoclave of a capacity of 2 liters equipped with a reflux condenser, a gas-blowing tube, a discharged tube, a temperature-measuring tube and an electromagnetic stirrer, 800 g of 93% acetic acid, 20 g of cobalt acetate tetrahydrate, 150 g of cerium acetate monohydrate, 0.6 g of ammonium bromide and 55 g of 2,6-DIPN were introduced. In the next step, the mixture was oxidized while maintaining the mixture at a temperature of 180° C. and blowing compressed air into the mixture at a rate of 600 liter/hour under a pressure of 20 kg/cm$^2$ and under stirring for about 6.5 hours.

After the reaction was over, the thus formed mixture was cooled to 60° C., and after collecting the deposited material by filtration, the collected material was washed with acetic acid and dried to obtain 46.5 g of the crude crystals.

On carrying out each of the analyses, it was found that the content of 2,6-NDCA in the crude crystals was 95.7%, the content of the heavy metal salt of trimellitic acid was 1.42%, the OD value of the 25% solution of the crude crystals in methylamine, which is the index of the content of the colored material, was 0.82 and the content of bromine was 148 ppm. The yield of 2,6-NDCA out of 2,6-DIPN was 79.5% on a molar basis.

COMPARATIVE EXAMPLE

Into the same reaction apparatus as in Example 1, 800 g of 93% acetic acid, 70 g of cobalt acetate tetrahydrate, 130 g of manganese acetate tetrahydrate, 6 g of ammonium bromide and 55 g of 2,6-DIPN were introduced and after bringing the content of the autoclave into reaction under the same conditions as in Example 1, the reaction mixture was treated in the same manner as in Example 1 to obtain 50.5 g of crude 2,6-NDCA.

On carrying out the same analyses as in Example 1 on the crude 2,6-NDCA, it was found that the purity was 78.5%, the content of bromine was 3765 ppm and the value of OD was 0.85. The yield of 2,6-NDCA out of 2,6-DIPN was 70.8% on a molar basis.

EXAMPLE 2

Into a 50 liter titanium-lined stainless steel autoclave equipped with a stirrer and a reflux condenser were supplied, 2,6-DIPN, 6-isopropyl-2-naphthoic acid (an oxidized intermediate of 2,6-DIPN), acetic acid, cobalt acetate tetrahydrate, cerium acetate monohydrate and ammonium bromide at the respective rates of 1000 g/hour, 20 g/hour, 6940 g/hour, 600 g/hour, 705 g/hour and 16 g/hour via the feed line (4) for the raw materials. Then, by introducing compressed air at a rate of 6 Nm$^3$/hour to the reactor (5) via the feed line (6), 2,6-DIPN and 6-isopropyl-2-naphthoic acid were oxidized at 180° C. under a pressure of 9 kg/cm$^2$.

The exhaust gas from the reactor (5) was cooled by the reflux condenser (8), and acetic acid and water contained in the exhaust gas were recycled to the reactor (5) via the line (9).

The oxidation product was continuously drawn through the line (11) and the pressure of the reaction was reduced to ordinary pressure in the flash vessel (12) and the temperature of the product went down to about 100° C. in the vessel (12). The solid material consisting mainly of 2,6-NDCA was separated by the centrifugal separator (13), washed with hot acetic acid of a rate of 2000 g/hour and sent to the drier (14) wherein about 600 g/hour of water-containing acetic acid were separated and recovered and 910 g/hour of dry, crude 2,6-NDCA crystals were obtained. The dry, crude 2,6-NDCA crystals were led to the catalyst-extracting vessel (16) via the line (15). The content of 2,6-NDCA in the crude crystals in the line (15) was about 85% by weight.

On the other hand, the filtrate and washing (about 10 kg/hour) from the centrifugal separator (13) were discharged via the drawing line (29) and most of them were led to the dehydrating tower (31) via the line (30) and after removing water (about 500 g/hour) formed by oxidation of 2,6-DIPN, they were returned to the dissolving vessel (3) of the raw materials.

About a third by volume of the liquid drawn from the bottom of the dehydrating tower (31) via hhe line (33) was led to the acetic acid-recovering tower (35) via the line (34) and acetic acid was recovered from the liquid, and most of the recovered acetic acid (2000 g/hour) was used for washing the cake in the centrifugal separator (13), and the rest was returned to the dissolving vessel (3) via the line (36). Further, the rest of the liquid remaining in the bottom of the dehydrating tower (31) was also returned to the vessel (3).

The residue drawn from the bottom of the acetic acid-recovering tower (35) contained a part of the catalyst and alkali-soluble organic by-products and was led to the catalyst-separating vessel (42) via the line (40).

On the other hand, into the dissolving vessel (3), 2,6-DIPN was added at a rate of 1000 g/hour via the line (1), and acetic acid, cobalt acetate tetrahydrate, cerium acetate monohydrate and ammonium bromide were added at the respective rates of 347 g/hour, 3 g/hour, 4 g/hour and 2 g/hour while utilizing the line (2) for make-up, and the thus introduced materials were dissolved at 80° to 90° C. under a nitrogen atmosphere.

Into the catalyst extracting vessel (16), 4% sulfuric acid was supplied at a rate of 2300 g/hour and it was stirred at 85° C. The slurry after finishing the extraction was subjected to solid-liquid separation in the centrifugal separator (18), and the solid matter was washed well with water at 80° C. (average amount of washing water being 1900 g/hour).

The content of water in the crude 2,6-NDCA crystals after being washed with water was about 45% by weight and the amount of the wet crystals was about 1500 g/hour. The crystals containing water were supplied to the salting-out vessel (20) via a solid-conveying apparatus (19), and an aqueous alkali solution containing 19% by weight of sodium chloride and 6% by weight of sodium hydroxide was supplied to the same vessel (20) at a rate of 4900 g/hour. Upon stirring the supplied materials in the vessel (20) at a temperature of 30° C., 2,6-NDCA.2Na was salted out. The slurry formed by the salting out was subjected to filtration in the filter press (22) and the obtained solid matter was washed with an aqueous 18% solution of sodium chloride. The filtrate of the filter press (22), through the line (47), was subjected to acid treatment in the vessel (50) and deposited impurities were removed by separator (51), and thereafter the filtrate was returned to the salting-out vessel (20) via the line (49).

The crystals obtained by salting out were dissolved in 5900 g/hour of water and after passing through the activated carbon tower (24) for decoloration via the line (23), the solution was supplied to the acid-treatment vessel (25). Separately, 30% sulfuric acid was supplied to the vessel (25), continuously at 1300 g/hour from the line (26) to control the pH of the content of the vessel (25) to lower than 3, thereby effecting acid-treatment (deposition of crystals from the solution by adding an acid). The milkwhite and gruel-like slurry formed by the acid-treatment was sent to the filter press (27), and after subjecting the slurry to solid-liquid separation, the solid matter was washed with 6000 g/hour of water and then continuously dried in a drier (28) at a temperature of 140° C. to obtain 2,6-NDCA of a high purity at a rate of 720 g/hour.

The filtrate from the filter press (a separator for the refined 2,6-NDCA) (27) was neutralized and then discharged through the line (48) to outside.

The purity of the obtained, purified 2,6-NDCA was 99.8% and the OD value (optical density) of the solution in methylamine, which represents the content of the colored component, was 0.013, and bromine was not detected in the purified 2,6-NDCA.

The yield of 2,6-NDCA of a high purity out of 2,6-DIPN supplied was 70.7% on a molar basis.

The filtrate from the extraction was sent to the catalyst-separating vessel (42) via the line (41) together with the residue from the bottom of the aeetic acid-recovering tower (35) via the line (40). Into the vessel (42), an aqueous 25% solution of sodium carbonate was continuously introduced from the line (43) while stirring the content of the vessel (42) to control the pH of the content thereof to 9.5, thereby depositing the mixture of basic carbonates of cobalt and cerium.

The slurry of basic carbonates of cobalt and cerium was subjected to solid-liquid separation by the centrifugal separator (44), and the filtrate was neutralized and then discarded via the line (46). The crystals were washed with water and then sent to the dissolving vessel (3) at an average rate of 30 g/hour, wherein the catalysts were stirred to be regenerated as the aceaate of cobalt and cerium.

EXAMPLE 3

Into a 50 liter titanium-lined stainless steel autoclave equipped with a stirrer and a reflux condenser were supplied 2,6-DIPN, 6-isopropyl-2-naphthoic acid (an oxidized intermediate of 2,6-DIPN), acetic acid, cobalt acetate tetrahydrate, manganese acetate tetrahydrate, cerium acetate monohydrate and ammonium bromide at the respective rates of 1000 g/hour, 20 g/hour, 6940 g/hour, 270 g/hour, 1310 g/hour, 230 g/hour and 7 g/hour via the feed line (4). Simultaneously compressed air was supplied at a rate of 6 $Nm^3$/hour to the reactor (5) via the feed line (6), and 2,6-DIPN and 6-isopropyl-2-naphthoic acid were oxidized at 180° C. under a pressure of 9 $kg/cm^2G$.

The exhaust gas from the reactor (5) was cooled by the reflux condenser (8), and acetic acid and water contained in the exhaust gas were recycled to the reactor (5) via the line (9).

The oxidation product was continuously drawn through the line (11) and the pressure of the reaction was reduced to ordinary pressure in the flash vessel (12) and the temperature of the product went down to about 100° C. in the vessel (12). The solid material consisting mainly of 2,6-NDCA was separated by the centrifugal separator (13), washed with hot acetic acid of a rate of 2000 g/hour and sent to the drier (14) wherein about 630 g/hour of water-containing acetic acid were separated and recovered, and 980 g/hour of dry, crude 2,6-NDCA crystals were obtained. The dry, crude 2,6-NDCA crystals were led to the catalyst-extracting vessel (16) via the line (15). The content of 2,6-NDCA in the crude crystals in the line (15) was about 85% by weight.

On the other hand, the filtrate and washings (about 11 kg/hour) from the centrifugal separator (13) were discharged via the drawing line (29) and most of them were led to the dehydrating tower (31) via the line (30) and after removing water (about 500 g/hour) formed by oxidation of 2,6-DIPN, they were returned to the dissolving vessel (3).

About a third by volume of the liquid drawn from the bottom of the dehydrating tower (31) via the line (33), was led to the acetic acid-recovering tower (35) via the line (34) and acetic acid was recovered from the liquid and most of the recovered acetic acid (2000 g/hour) was used for washing the cake in the centrifugal separator (13), and the rest was returned to the dissolving vessel (3) via the line (36). Further, the rest of the liquid remaining in the bottom of the dehydrating tower (31) was also returned to the vessel (3).

The residue drawn from the bottom of the acetic acid-recovering tower (35) contained a part of the catalyst and alkali-soluble oraanic by-products and was led to the catalyst-separating vessel (42) via the line (40).

On the other hand, into the dissolving vessel (3), 2,6-DIPN was added at a rate of 1000 g/hour via the line (1), and acetic acid, cobalt acetate tetrahydrate, manganese acetate tetrahydrate, cerium acetate monohydrate and ammonium bromide were added at the respective rates of 347 g/hour, 2 g/hour, 5 g/hour, 2 g/hour and 1.3 g/hour while utilizing the line (2) for make up, and the thus introduced materials were dissolved at a temperature of 80° to 90° C. under a nitrogen atmosphere.

Into the catalyst-extracting vessel (16), 4% sulfuric acid was supplied at a rate of 2300 g/hour and it was stirred at a temperature of 85° C. The slurry after finishing the extraction was subjected to solid-liquid separation in the centrifugal separator (18) and the solid matter was washed well with water at 80° C. (average amount of washing water being 1900 g/hour).

The content of water in the crude 2,6-NDCA crystals after being washed with water was about 45% by weight and the amount of the wet crystals was about 1600 g/hour. The crystals containing water were supplied to the salting-out vessel (20) via a solid-conveying apparatus (19), and an aqueous alkali solution containing 19% by weight of sodium chloride and 6% by weight of sodium hydroxide was supplied to the same vessel (20) at a rate of 4900 g/hour. Upon stirring the supplied materials in the vessel (20) at a temperature of 30° C., 2,6-NDCA.2Na was salted out. The slurry formed by the salting out was subjected to filtration in the filter press (22) and the obtained solid matter was washed with an aqueous 18% solution of sodium chloride. The filtrate of the filter press (22), through the line (47), was subjected to acid treatment in the vessel (50) and deposited impurities were removed by separator (51), and thereafter it was returned to the salting-out vessel (20) via the line (49).

The crystals obtained by salting out were dissolved in 6000 g/hour of water and after passing through the activated carbon tower (24) for decoloration via the line (23), the solution was supplied to the acid-treatment vessel (25). Separately, 30% sulfuric acid was supplied to the vessel (25) continuously at a rate of 1300 g/hour from the line (26) to control the pH of the content of the vessel (25) to lower than 3, thereby effecting acid-treatment. The milk-white and gruel-like slurry formed by the acid-treatment was sent to the filter press (27), and after subjecting the slurry to solid-liquid separation, the solid matter was washed with 6000 g/hour of water and then continuously dried in the drier (28) at a temperature of 140° C. to obtain 2,6-NDCA of a high purity at a rate of 760 g/hour.

The filtrate from the filter press (a separator for the purified 2,6-NDCA) (27) was neutralized and then discharged through the line (48) to outside.

The purity of the obtained, purified 2,6-NDCA was 99.8% and the OD value of the solution in methylamine, which represents the content of the colored component, was 0.012.

Bromine was not detected in the purified 2,6-NDCA.

The yield of 2,6-NDCA of a high purity out of 2,6-DIPN supplied was 77.5% on a molar basis.

The filtrate from the extraction, which was sulfuric acid-acidic and contained the catalyst, and the washings were sent to the catalyst-separating vessel (42) via the line (41) together with the residue from the bottom of the acetic acid-recovering tower (35) via the line (40). Into the vessel (42), an aqueous 25% solution of sodium carbonate was continuously introduced from the line (43) while stirring the content of the vessel (42) to control the pH of the content thereof to 9.5, thereby depositing the mixture of basic carbonates of cobalt, manganese and cerium.

The slurry of basic carbonates of cobalt, manganese and cerium was subjected to solid-liquid separation by the centrifugal separator (44), and the filtrate was neutralized and then discarded via the line (46). The crystals were washed with water and then sent to the dissolving vessel (3) at an average rate of 30 g/hour, wherein the catalysts were stirred to be regenerated as the acetate of cobalt, manganese and cerium.

EXAMPLE 4

Into a glass autoclave of an inner volume of 1 liter, 350 g of methanol and 50 g of crude 2,6-NDCA were introduced and while stirring the content of the autoclave, 11 g of concentrated sulfuric acid were added into autoclave, and the reaction was carried out after raising the temperature of the content to 127° to 130° C. under a pressure for 5 hours. After the reaction was over, the content of the autoclave was cooled to 30° C., and the deposited crystal of dimethyl ester of 2,6-NDCA were separated from the reaction mixture and washed with 80 g of methanol. Upon drying the crystals at a temperature of 120° C., 47.3 g of dimethyl ester of 2,6-NDCA were obtained. The purity of the dimethyl ester of 2,6-NDCA was 98.1% and the yield thereof out of the crude 2,6-NDCA was 92.0% on a molar basis.

What is claimed is:

1. A process for producing 2,6-naphthalenedicarboxylic acid by oxidation of 2,6-diisopropylnaphthalene, comprising the steps of:

(a) dissolving 2,6-diisopropylnaphthalene or an oxidized intermediate thereof and a catalyst comprising a water-soluble salt of cobalt, a water-soluble salt of manganese or a mixture thereof, a water-soluble salt of cerium and a bromine compound in a lower aliphatic monocarboxylic acid as the solvent, wherein the concentration of 2,6-diisopropylnaphthalene in the solvent is less than 20% by weight and the molar ratio of 2,6-diisopropylnaphthalene to the metals of the catalyst is less than 2.5, the atomic ratio of cobalt, manganese or a mixture thereof to cerium is from 0.0001 to 0.1 and the total amount of heavy metals in said catalyst is from 0.01 to 0.15 g-atom per 100 g of said lower aliphatic monocarboxylic acid;

(b) continuously supplying the solution prepared in step (a) to an oxidation reactor and oxidizing 2,6-diisopropylnapthhalene or the oxidized intermediate thereof with molecular oxygen at a reaction temperature of 140° to 210° C. under a partial pressure of oxygen of 0.2 to 8 kg/cm² (absolute pressure);

(c) continuously with drawing the reaction mixture obtained in step (b) from the oxidation reactor, depositing crystals of the crude 2,6-naphthalenedicarboxylic acid from the reaction mixture nnd separating the crystals;

(d) bringing the crystals into contact with an aqueous solution of mineral acid by adding an aqueous solution of sulfuric acid or hydrochloric acid of a concentration from 1 to 10% by weight to the crude 2,6-naphthalenedicarboxylic acid under stirring while adjusting the pH of the aqueous solution form 1 to 3, thereby dissolving and removing the metals of the catalyst from the crystals;

(e) purifying the crude 2,6-naphthalenedicarboxylic acid crystals and, optionally, (f) converting to dialkali salt to the free acid of 2,6-naphthalenedicarboxylic acid;

(g) adding an aqueous solution of an alkali carbonate or an alkali bicarbonate of a concentration of 1 to 34% by weight to the filtrate of step (d) to adjust pH of the filtrate of step (d) from 7 to 10, thereby precipitating heavy metals of the catalyst as carbonates of bicarbonates, separating the carbonates or bicarbonates and supplying them to the first step, and (h) supplying the filtrate of step (c) to step (a).

2. The process according to claim 1, in which the crude crystals are purified in step (e) by adding the crude 2,6-naphthalenedicarboxylic acid crystals to methanol, adding concentrated sulfuric acid to the mixture under stirring, bringing the mixture into reaction under heating, thereby transforming 2,6-naphthalenedicarboxylic acid into dimethyl 2,6-naphthalenedicarboxylate, cooling the reaction mixture, thereby precipitating and separating the purified dimethyl 2,6-naphthalene dicarboxylate.

3. The process according to claim 1, in which the crude crystals in step (e) are purified crystals of dialkali 2,6-naphthalenedicarboxylate by applying a water-soluble alkali and a water-soluble neutral salt which has a common cation as that of said water-soluble alkali, and then converting the crystals of dialkali 2,6-naphthalenedicarboxylate to the crystals of 2,6-naphthalenedicarboxylic acid by dissolving the purified dialkali 2,6-naphthalenedicarboxylate in water, adding a mineral acid to the aqueous solution adjusting its pH to less than 4, and precipitating and separating the purified crystals of 2,6-naphthalnedicarboxylic acid.

4. The process according to claim 3, in which the crude crystals ar purified in step (e) by dissolving the crude 2,6-naphthalenedicarboxylic acid crystals in 2 to 10 wt % aqueous water-soluble alkali solution of pH of higher than 9 containing said water-soluble alkali in an amount of more than the neutralization equivalent, adding a water-soluble neutral salt of the same cation as that of the water-soluble alkali, or 10 to 30 wt % aqueous solution thereof, and precipitating and separating dialkali 2,6-naphthalenedicarboxylate, the concentration of said crude 2,6-naphthalenedicarboxylic acid crystals in the aqueous water-soluble alkali solution or the aqueous solution of the water-soluble alkali and water-soluble neutral salt being 50 to 250 g/liter, and when step (e) is carried out at 10° to 100° C. under stirring.

5. The process according to claim 3, in which the crude 2,6-naphthalenedicarboxylic crystals are purified in step (e) by adding the crude 2,6-naphthalenedicarboxylic acid crystals to an aqueous solution containing more than the neutralization equivalent amount of a water-soluble alkali and a water-soluble neutral salt having the same cation as that of the water-soluble alkali, thereby precipitating and separating dialkali 2,6-naphthalenedicarboxylate.

6. The process according to claim 3, in which the mineral acid in step (d) is selected from the group consisting of sulfuric acid, hydrochloric acid and nitric aoid, and is added as an aqueous solution, having a concentration of 5 to 60% by weight, to the aqueous solution of dialkali 2,6-naphthalenedicarboxylate.

7. The process according to claim 3, in which said water-soluble alkali is selected from the group consisting of sodium hydroxide, potassium hydroxide, sodium carbonate and potassium carbonate.

8. The process according to claim 3, in which said water-soluble alkali is selected from the group consisting of sodium hydroxide, potassium hydroxide, sodium carbonate and potassium carbonate.

9. The process according to claim 3, wherein said water-soluble alkali and water-soluble neutral salt are sodium hydroxide and sodium chloride, respectively.

10. The process according to claim 3, in which the aqueous solution of the purified dialkali 2,6-naphthalenedicarboxylate is subjected to adsorption treatment by activated carbon before the mineral acid is added.

11. The process according to claim 1, in which the crude 2,6-naphthlenedicarboxylic acid crystals, separated in step (c) are washed with a lower aliphatic monocarboxylic acid containing less than 30 wt % of water and then heated at the temperature between the boiling point of the monocarboxylic acid and 200° C. to recover the monocarboxylic acid.

12. The process according to claim 11, in which aliphatic monocarboxylic acid is acetic acid and the washed crystals are heated at the temperature of 120° to 200° C.

13. The process according to claim 1, in which a portion of the filtrate in step (c) is recycled to step (a) and the balance of the filtrate is dehydrated to remove by-produce water and recycled also to step (a).

14. The process according to claim 13, in which a portion of the dehydrated filtrate is supplied to a lower aliphatic monocarboxylic acid-recovering tower and a portion of the monocarboxylic acid recovered is recycled to step (a) and the balance is supplied to the crude 2,6-naphthalenedicarboxylic acid crystal separator to wash the crystals.

15. The process according to claim 4, in which the aqueous alkali solution of the crude 2,6-naphthalenedicarboxylic acid of step (e) is subjected to adsorption treatment by activated carbon before the water-soluble neutral salt is added.

16. The process according to claim 14, in which residue from the bottom of the recovering tower is supplied to step (g) together with the filtrate of step (d).

* * * * *